United States Patent
Austring et al.

(10) Patent No.: US 6,540,760 B2
(45) Date of Patent: Apr. 1, 2003

(54) CUTTING BLADE AND CUTTING BLADE ASSEMBLY

(75) Inventors: Robert Austring, Rancho Cucamonga, CA (US); William Hagel, So. Pasadena, CA (US); Michael J. Ram, Bell Canyon, CA (US)

(73) Assignee: Oasis Medical, Inc., Glendora, CA (US)

( * ) Notice: Subject to any disclaimer, the term of this patent is extended or adjusted under 35 U.S.C. 154(b) by 5 days.

(21) Appl. No.: 09/884,314

(22) Filed: Jun. 19, 2001

(65) Prior Publication Data

US 2003/0004526 A1 Jan. 2, 2003

Related U.S. Application Data

(60) Provisional application No. 60/231,964, filed on Jun. 23, 2000.

(51) Int. Cl.$^7$ .................................................. A61F 9/00
(52) U.S. Cl. .................... 606/166; 606/167; 606/178
(58) Field of Search ................................. 606/166, 167, 606/169, 176, 177, 178; 30/346, 346.5, 346.57, 337, 339; 56/299

(56) References Cited

U.S. PATENT DOCUMENTS

| | | | |
|---|---|---|---|
| 2,457,772 A | 12/1948 | Brown et al. | 128/305.5 |
| 3,428,045 A | 2/1969 | Kratzsch et al. | 128/305 |
| 3,852,881 A | * 12/1974 | Treace | 606/178 |
| 3,952,412 A | * 4/1976 | Rhodes | 606/178 |
| 4,223,514 A | * 9/1980 | Halls et al. | 56/299 |
| 4,665,914 A | 5/1987 | Tanne | 128/305 |
| 4,807,623 A | 2/1989 | Lieberman | 128/305 |
| 4,884,570 A | 12/1989 | Krumeich et al. | 128/305 |
| 4,917,086 A | 4/1990 | Feltovich et al. | 606/132 |
| 5,133,726 A | 7/1992 | Ruiz et al. | 606/166 |
| 5,201,747 A | 4/1993 | Mastel | 606/167 |
| 5,203,865 A | 4/1993 | Siepser | 606/166 |
| 5,222,967 A | 6/1993 | Casebeer et al. | 606/166 |
| 5,224,950 A | 7/1993 | Prywes | 606/166 |
| 5,336,235 A | 8/1994 | Myers | 606/166 |
| 5,337,482 A | 8/1994 | Schmidt | 30/162 |
| 5,342,378 A | 8/1994 | Giraud et al. | 606/166 |
| 5,405,355 A | 4/1995 | Peyman et al. | 606/166 |
| 5,486,188 A | 1/1996 | Smith | 606/166 |
| 5,496,339 A | 3/1996 | Koepnick | 606/166 |
| 5,591,174 A | 1/1997 | Clark et al. | 606/130 |
| 5,595,570 A | 1/1997 | Smith | 606/166 |
| 5,603,365 A | 2/1997 | Stewart | 144/230 |
| 5,619,889 A | 4/1997 | Jones et al. | 76/104.1 |
| 5,658,303 A | 8/1997 | Koepnick | 606/166 |
| 6,051,009 A | 4/2000 | Hellenkamp et al. | 606/166 |

FOREIGN PATENT DOCUMENTS

| | | | |
|---|---|---|---|
| DE | 3147662 | 9/1983 | A61F/9/00 |
| WO | WO 9306783 | 4/1993 | A61B/17/32 |
| WO | WO 9926568 | 3/1999 | A61F/9/007 |

* cited by examiner

Primary Examiner—Julian W. Woo
(74) Attorney, Agent, or Firm—Koppel, Jacobs, Patrick & Heybl; Michael J. Ram

(57) ABSTRACT

A blade and a blade assembly wherein the blade has a front, beveled, sharpened edge, two side edges meeting at a point spaced from the front edge and at least one attachment structure extending outwardly from each side edge. A blade holder, which extends beyond the side edges and attachment structures of the blade, sits on a top surface of the blade and is attached to the blade by a portion thereof which receives the attachment structures. The holder has an opening in an exposed surface to receive an extension from a drive mechanism such that when the drive mechanism is activated the blade is caused to vibrate or oscillate. The blade is oscillated in a lateral fashion when driven by a rod rotating along a circular path.

20 Claims, 5 Drawing Sheets

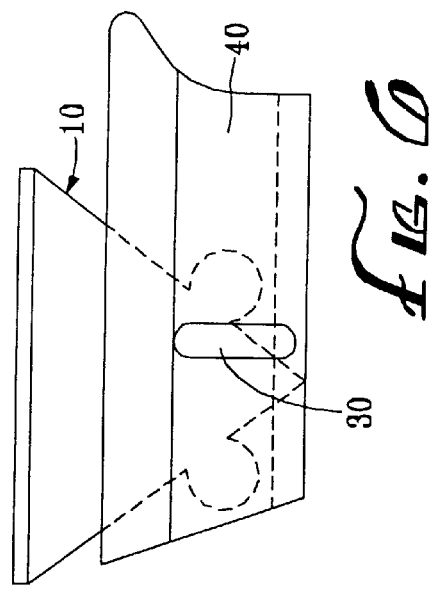
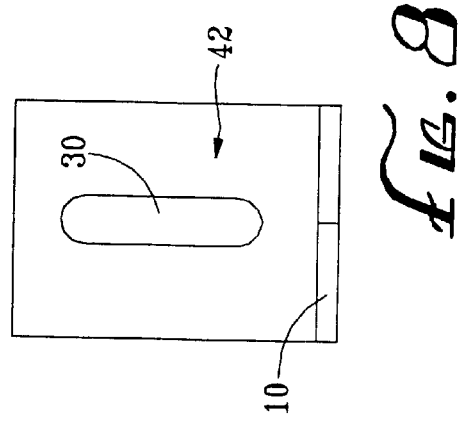
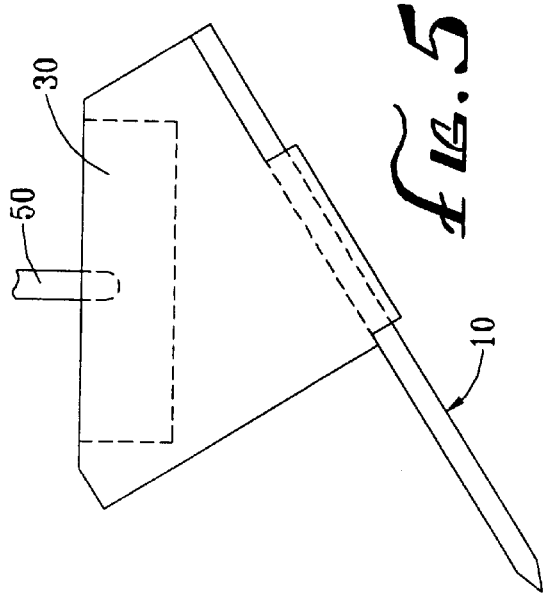
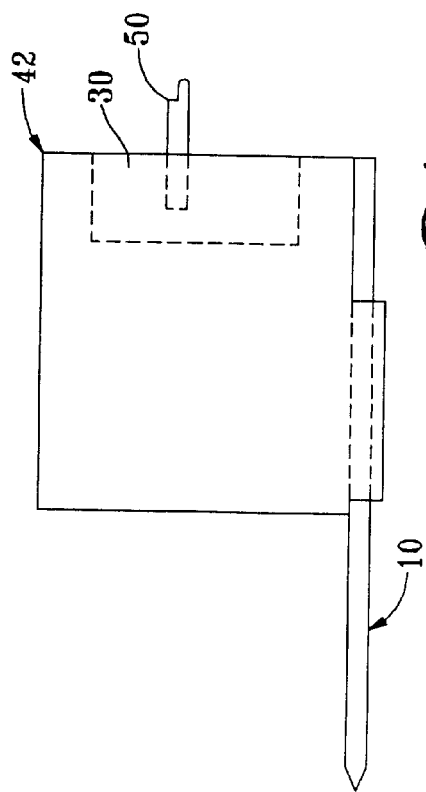

CUTTING BLADE AND CUTTING BLADE ASSEMBLY

This application is based on Provisional Application 60/231,964 filed Jun. 23, 2000. Applicant claims priority from the filing date of said Provisional Application.

BACKGROUND OF THE INVENTION

The invention relates to a blade, and a holder for that blade, for use in a manual or automated surgical device used for cutting the cornea of the eye and particularly for forming a corneal flap. Several surgical devices are currently available for cutting corneal tissue or a circular flap in the cornea around the pupil of the eye. These devices, commonly referred to as microkeratomes, are placed on the cornea and held in place by suction applied to the periphery of the cornea. A disposable blade is placed into the device and the sharpened edge of the blade is advanced at a precise angle and a predetermined depth into the corneal tissue. The device then provides for a vibrating or oscillating motion to the blade and allows the blade to be moved in a circular, linear, or curvilinear path around the central axis of the microkeratome. This results in the cornea being cut to raise a thin circular layer of anterior cornea with the incision being from about 100 to 200 micron, in depth and about 10 mm in diameter. In a more recent procedure, referred to as LASIK surgery, the circular corneal incision is combined with laser sculpting of a portion of the cornea.

Several microkeratomes are shown in the patent literature. U.S. Pat. No. 5,624,456 covers a device offered by Bausch & Lomb, known as the Hansatome, and U.S. Pat. No. 6,051,009 is directed to blades specifically designed for use in the device shown in the '456 patent.

Other patents to microkeratomes of different designs are shown in U.S. Pat. Nos. 5,496,339 and 5,658,303 to Koepnick, U.S. Pat. No. 4,884,570 to Krumeich, U.S. Pat. Nos. 5,501,174 and 5,591,174 to Clark et al, U.S. Pat. No. 5,342,378 to Giraud et al, U.S. Pat. No. 6,022,365 to Aufaure et al, U.S. Pat. No. 5,133,726 to Ruiz et al, and U.S. Pat. No. 4,662,370 to Hoffmann et al. All operate in generally the same manner and all require a disposable blade be inserted therein. However, each device requires a different shaped blade and/or blade with blade holder. Therefore, there is a value in having a disposable blade configuration, which may have varied dimensions, which can be assembled with a suitable blade holder for each different device, using the same assembly techniques, so as to provide ease of manufacturing and uniformity of surgical outcome irrespective of the instrument into which the blade or blade assembly is placed.

SUMMARY OF THE INVENTION

The invention comprises a blade and a blade assembly wherein the blade has a front, beveled, sharpened edge, and two side edges meeting at a point spaced from the front edge. At least one attachment structure extends from each side edge. A blade holder which extends beyond the side edges, sits on a top surface of the blade and is attached to the blade by a portion thereof which receives the attachment structure. The holder has an opening in an exposed surface to receive an extension from a drive mechanism such that when the drive mechanism is activated the blade is caused to vibrate of oscillate.

DESCRIPTION OF THE FIGURES

FIG. 5 is a side view of a second embodiment of a blade assembly including the blade of FIG. 1.

FIG. 6 is a top view of the second embodiment of the blade assembly of FIG. 5.

FIG. 7 is a side view of a third embodiment of a blade assembly including the blade of FIG. 1.

FIG. 8 is a rear view of the third embodiment of the blade assembly of FIG. 7.

DETAILED DESCRIPTION OF THE INVENTION

Figure 1:
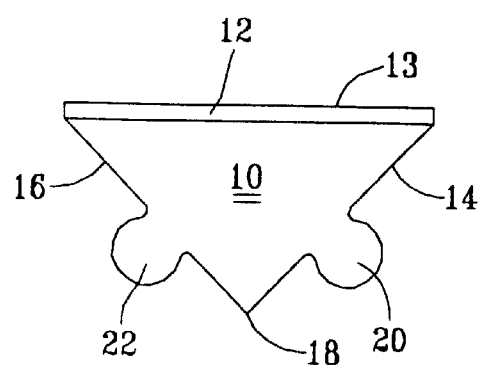
FIG. 1 is bottom view of a blade incorporating features of the invention.
Figure 9:
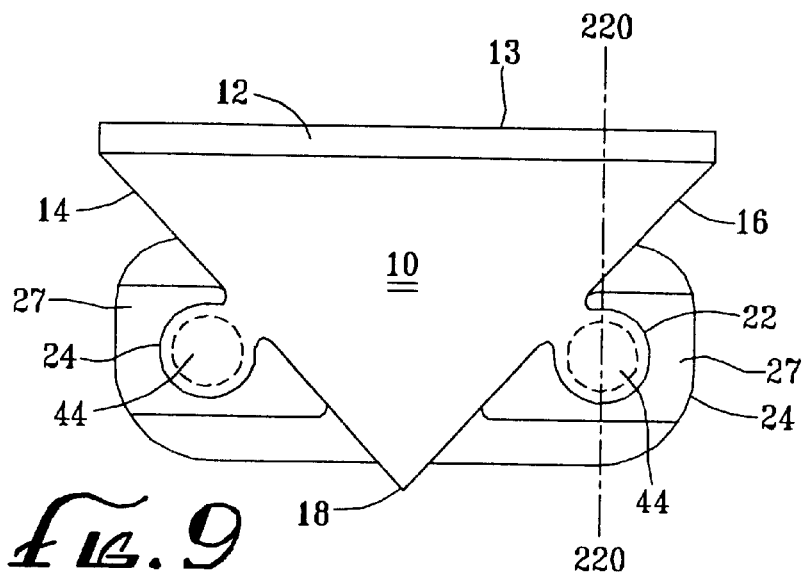
FIG. 9 is a bottom view of a variation of the assembled embodiment of FIG. 4.

FIG. 1 shows a top view of a blade incorporating features of the invention. As shown in FIG. 1, the blade 10, in a preferred embodiment fabricated of a flat surgical steel about 0.01 inches thick, is in the shape of a triangle with a forward portion 12 beveled to a sharp edge 13. The various triangular embodiments have a forward portion from about 0.45 to about 0.53 inches in width. The triangular blade has a dimension from the forward portion 12 to the point 18 from about 0.27 to about 0.32 inches. The two side edges 14, 16 of the blade meet at a point 18 spaced from the front edge 12. Extending from each of the side edges 14, 16 are extensions 20, 22, generally in the plane of the blade. In the embodiment shown in the figures, the extensions 20, 22 are circular in shape, the circular extensions intersecting the first and second side edges 14, 16 of the blade. In a preferred construction, the circular extension 20, 22 have at least about 180° of the circumference extending from the blade. FIGS. 1 and 9 have about 270° of the circumference in the extension while the remaining 90° constitutes the intersection of the extensions 20, 22 with the blade side edges 14, 16.

Figure 2:
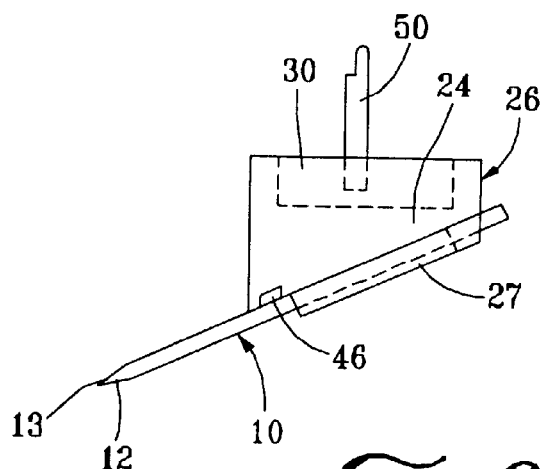
FIG. 2 is a side view of a first embodiment of a blade assembly including the blade of FIG. 1.
Figure 3:
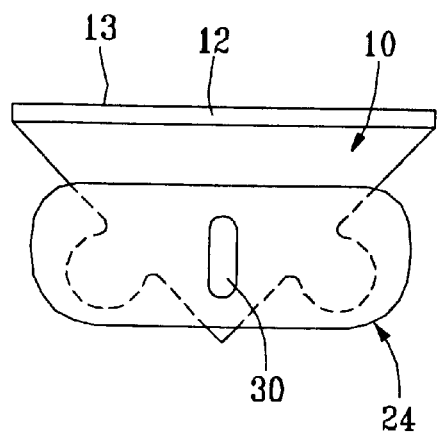
FIG. 3 is a top view of the first embodiment of the blade assembly of FIG. 2.
Figure 4:
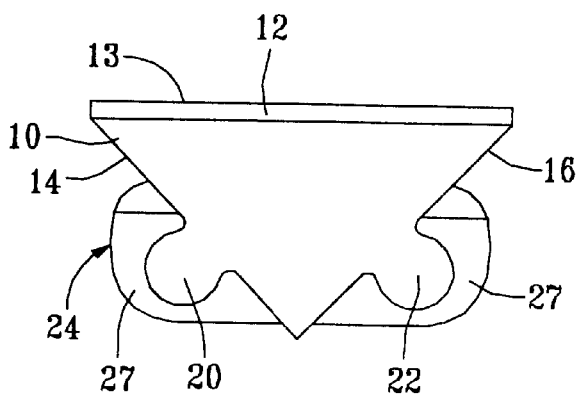
FIG. 4 is a bottom view of the first embodiment of the blade assembly of FIG. 2.
Figure 12:
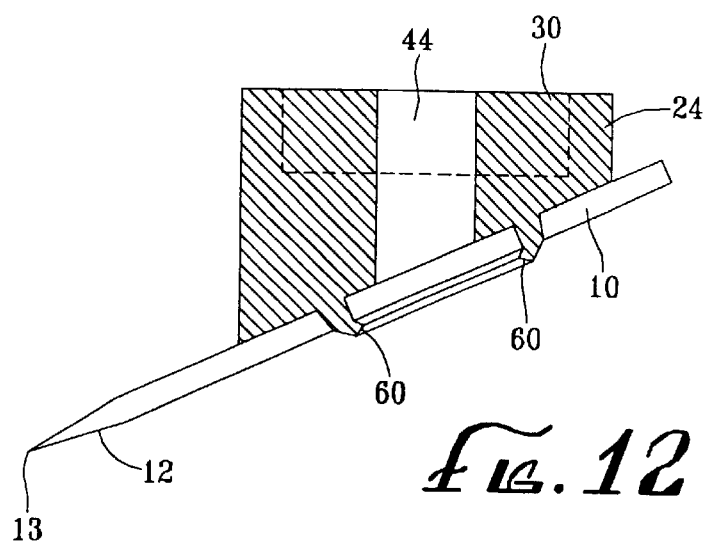
FIG. 12 is a cutaway side view along line 220–220 of FIG. 9.

In order to adapt the various blades 10 to operate with the various different microkeratomes the blade is generally attached to a holder to form a blade assembly, the holder being designed to receive a drive mechanism. FIGS. 2, 3 and 4 show a side, top and bottom view of a first embodiment of the blade of FIG. 1 attached to a blade holder 24 to form a blade assembly 26. The blade holder is typically formed of a machined or molded plastic material. As best shown in FIG. 4 and the variation of FIG. 10, the bottom surface 28 of the blade holder 24 has an indented blade receiving portion 25 with raised areas 27 on either side of the indented area sized and shaped to receive the extensions 20, 22 as well as a portion of the blade itself. A circular extension 20, 22 extending more than 180° in arc is preferred as this provides a self centering function when the blade is attached to the blade 24 holder by various assembly techniques. The blade 10 is retained in the indented blade receiving portion 25 in the blade holder 24 by an adhesive, cold staking, heat staking, over moldings, or snap (detent) fit means. Snap (dent) fittings utilizes a receiving portion with an angled edges 60 as shown in FIG. 12. Alternatively, a preformed blade 10 may be molded into the plastic blade holder 24 when it is formed. Also, the bottom surface of the blade holder 24 is at an angle to the plane of the top surface, typically 10° to 45°, so that the blade rests at a desired angle to horizontal when placed in the microkeratome. Alternatively, a separate bottom (not shown) can be applied to the blade holder 24 to sandwich the blade 10 between the holder 24 and the bottom cover.

As shown in FIG. 3, the blade holder 24 has a non-circular aperture 30 in the top thereof to receive a drive mechanism 50. Typically, as shown in several of the patents cited above and incorporated herein by reference, the drive mechanism 50 is a rod offset mounted on a rotating shaft. The rod has a diameter substantially the same as the width of the aperture 30. Rotation of the shaft causes the rod to rotate in a circular path, which in turn causes lateral oscillation of the blade assembly in the microkeratome. This oscillating motion is intended to improve the quality of the cut made by the sharp edge 13 of the blade 10. In this instance, the drive mechanism 50 enters the aperture 30 in a substantially vertical manner but at an angle to the plane of the blade. This embodiment is designed for use in a microtome manufactured by Bausch & Lomb and referred to as the HANSATOME™.

FIGS. 5 and 6 are to a second embodiment of the blade assembly which incorporates the blade 10 of FIG. 1 with a different designed blade holder 40 for use in the C-B™ microkeratome manufactured by Moria. This blade assembly also receives a substantially vertical drive mechanism 50. However, because the aperture 30 can be a slot or oval, the blade assembly can receive a drive mechanism 50 mounted in other than a vertical manner and still function in substantially the same manner.

FIGS. 7 and 8 show a third embodiment designed to receive a drive from other than the vertical. The drive 50 may in fact be parallel to the plane of the blade, as shown in some of the above referenced patents. In such an instance, the blade may be held in the keratome at an angle to the vertical, or horizontal. Like components are numbered the same as in the prior figures.

Figure 10:
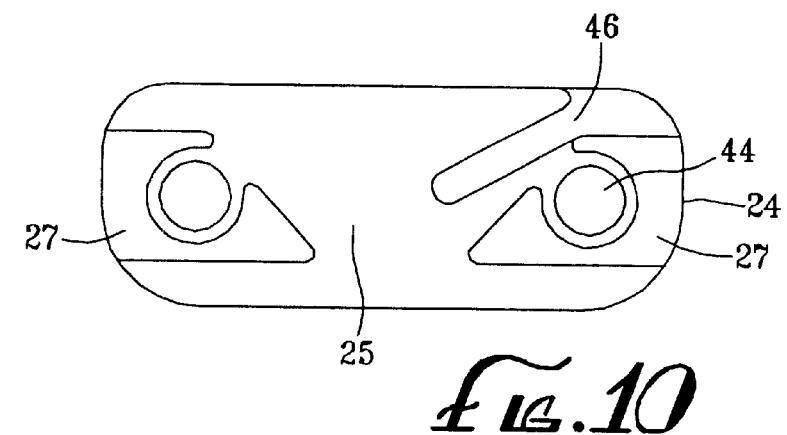
FIG. 10 is a bottom view of the blade holder of the variation of FIG. 9.
Figure 11:
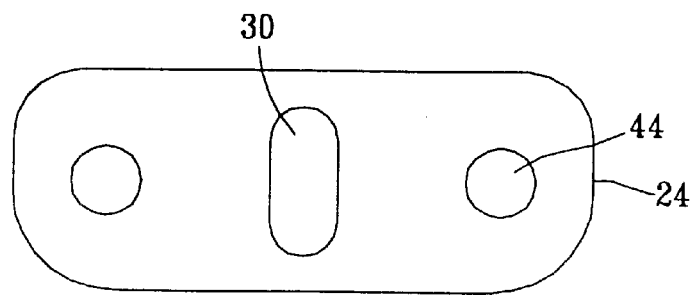
FIG. 11 is a top view of the blade holder of the variation of FIG. 9.

A variation of the blade of FIG. 1 and the holder of FIGS. 2–4 is shown in FIGS. 9–11. In this variation the holder 24 has holes 44 therethrough. While the hole 44 has been shown as round, any shape hole can be used. The purpose of the hole 44 in the holder 24 is to assure proper alignment of the holder 24 on a machining fixture (not shown) when the holder 24 is positioned or refixtured for the machining of the indented blade receiving portion 25. This assures proper location or registration of the blade with the slot 30 in the assembled product.

As shown in FIGS. 2 and 10, the blade holder 24 can also have a groove 46 therein so that one blade of a forceps or tweezer can be inserted therein to grasp the blade 10 for placement of the blade 10 with attached blade holder 24 in to the microkeratome.

While FIG. 1 shows the extensions 20, 22 as circular pieces extending from the sides, the extensions can be of various different shapes designed to mate with a like shape in the holder.

While shown to be in the plane of the blade 10, the extensions 20, 22 can also be at an angle to the plane or be perpendicular to the plane for insertion in matching holes extending into the holder. It is also contemplated that the blade may be fabricated from a material other than stainless steel, such as ceramics, zirconium, sapphire or similar material, or may have coatings on the beveled front edge to aid in creating a smooth cut in the corneal tissue. It is also possible for the blade and blade holder to be fabricated as a single piece with front edge treated to produce a suitable cutting surface or to receive a cutting component, such as a sapphire, or diamond, ceramic or zirconium, cutting edge, such as typically used in other ophthalmic tissue cutting tools. A typical material for construction of the blade holder is acetal (Delrin®), nylon or other engineering plastics which can be formed or machined into structures with dimensions having controlled tolerances. It is also possible that the holder and blade could be formed of a single engineering plastic, capable of forming or being formed into a sharp forward blade edge. Still further, the whole assembly could be of a hard material, such as a ceramic material, which can be honed to a sharp edge.

FIGS. 13–16 show additional embodiments of the blade. The overall shape of the blade 100 is parabolic with a front portion thereof removed to form a sharp front edge 13. The blade 100 is placed in a holder 124 fabricated with an indented portion for receiving the blade 100 with extensions 20, 22 in the manner as described in the regard to the embodiments described above.

As set forth above, the extensions 20, 22 can be of any shape. Also, if they are circular extensions, they preferably include at least about 180° of arc to provide a secure registration of the blade in the holder. The dimensions of the parabolic shape of the blade can be varied.

Still further, the blade shape does not have to be parabolic or circular but can be oval (elliptical) in shape or have a compound curved surface. It can also have more than two extensions.

Figure 13:
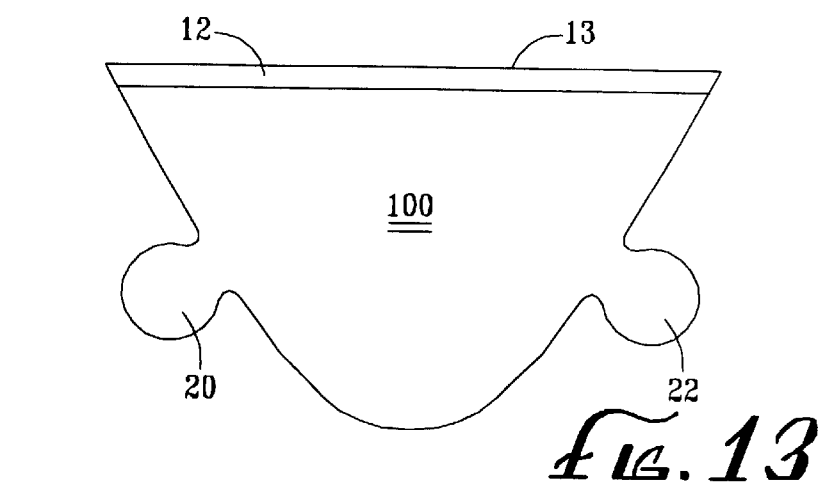
FIG. 13 is a top view of an alternative blade design having a parabolic shape.
Figure 14:
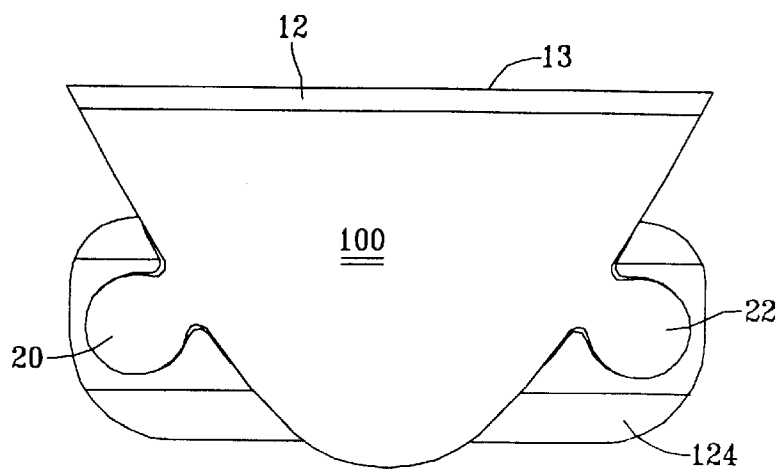
FIG. 14 is a bottom view of the blade of FIG. 13 mounted in a blade holder.

FIG. 14 shows the blade of FIG. 13 in the blade holder 24.

Figure 15:
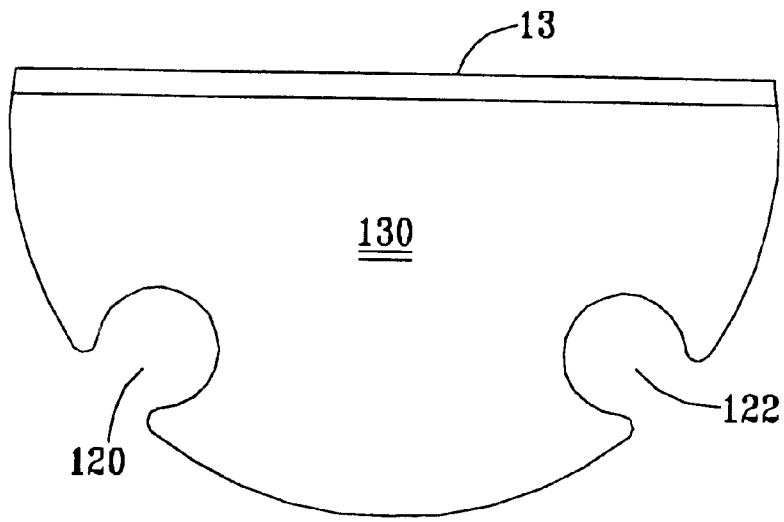
FIG. 15 is a top view of an alternative blade design with a semicircular shape having circular retention means within the periphery of the blade.
Figure 16:
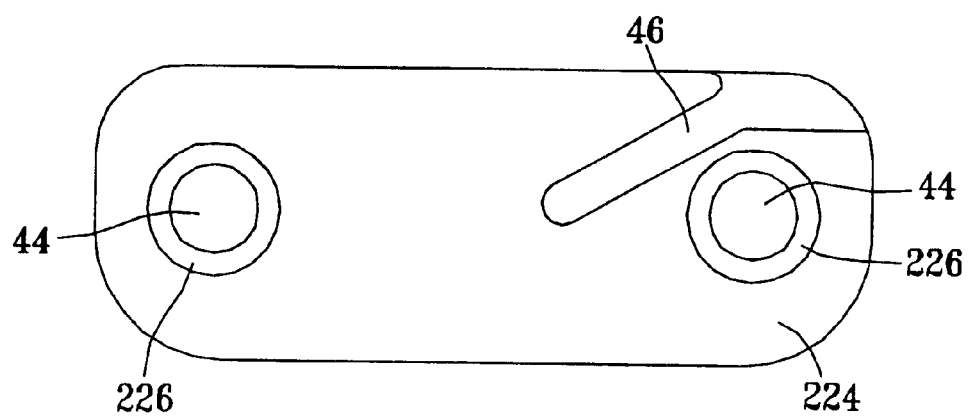
FIG. 16 is a top view of a blade holder for receiving the blade of FIG. 15.

A still further variant, shown in FIG. 15, is a circular blade 130 with cut off front portion and, rather than circular extensions, circular incursions 120, 122 in the circumferential walls. FIG. 16 is a holder designed to receive the blade of FIG. 15. Instead of including a indented receiving portion as in the prior described embodiments, this blade shows an alternative holding mechanism which incorporates circular extensions 226 which are inserted in the blade incursions 120, 122 to secure the blade 130 to the blade holder 224. The attachment techniques discussed above can also be used.

We claim:

1. A blade assembly for use in a surgical device that cuts at least partially across the cornea of an eye of a patient, the surgical device including means attachable to the cutting blade assembly to cause a forward cutting edge of the blade assembly to vibrate or oscillate, the cutting blade assembly comprising:

a) a triangular shaped cutting blade comprising a forward portion constituting a first side of the triangular shaped cutting blade and first and second rearwardly extending side edges constituting a second and third side of the triangular shaped cutting blade, the front portion comprising a sharp, cutting edge in the plane of the blade and extending across the width thereof, the triangular shaped blade also including a first and a second extension projecting outwardly from the first and second side edges, respectively, and b) a blade holder having a driving mechanism receiving portion and an blade receiving portion, the blade receiving portion sized and shaped to receive the triangular shaped blade and extensions with the sharp edge of the front portion extending beyond a front surface of the blade holder, the triangular blade being secured within the blade receiving portion of the blade holder.

2. The blade assembly of claim 1 wherein the blade receiving portion of the blade holder comprises an indented area on a face of the blade holder, the indented area being located between two spaced apart raised areas, the raised areas being located in contacting relationship with the first and second side edges of the cutting blade.

3. The blade assembly of claim 1 wherein the extensions on the blade are circular and have a circumference at least about 180° of a circle.

4. The blade assembly of claim 1 wherein the extensions on the blade project outwardly in the plane of the blade.

5. The blade assembly of claim 1 wherein the blade holder has registration means therein, for use in reproducible positioning in the blade holder for machining the blade holder and reproducibly placing the blade in the blade holder.

6. The blade assembly of claim 5 wherein the registration means in the blade holder comprises a hole in the blade holder shaped and sized to temporarily receive a like shaped and sized positioning in for machining.

7. The blade assembly of claim 1 wherein the blade is secured to the blade holder by a pressing the blade with extensions into the like-sized and shaped indentation in the face of the blade holder.

8. The blade assembly of claim 1 wherein the blade receiving portion has extended upper edges for snap fitting of the blade therein.

9. The blade assembly of claim 7 wherein the blade is further secured to the blade holder by an adhesive.

10. The blade assembly of claim 1 wherein the blade is secured to the blade holder by molding a preformed blade into the blade holder during formation of the blade holder.

11. The blade assembly of claim 1 wherein the blade holder includes a cutout portion on the face thereof for receiving a grasping portion of an instrument used to grasp the blade during placement into and removal of the blade and blade holder into a surgical instrument.

12. The blade assembly of claim 1 wherein the driving means receiving portion comprises an aperture in a second surface of the blade holder, said aperture being oriented to receive the driving means of the surgical device in a pre-designed orientation to the plane of the blade.

13. The blade assembly of claim 12 wherein the second surface of the blade holder is 10° to 45° to a plane parallel to the plane of the blade.

14. The blade assembly of claim 12 wherein the second surface of the blade holder is 10° to 45° to a plane perpendicular, to the plane of the blade.

15. A blade assembly for use in a surgical device that cuts at least partially across the cornea of an eye of a patient, the surgical device including means attachable to the cutting blade assembly to cause a forward cutting edge of the blade assembly to vibrate or oscillate, the cutting blade assembly comprising:

a) a cutting blade having a straight forward portion constituting a first side and a rear portion constituting a circular shaped circumferential edge extending rearwardly, the forward portion comprising a sharp cutting edge in the plane of the blade extending across the width thereof, the circular shaped blade having first and a second attachment means thereon or therein, and b) a blade holder having a driving mechanism receiving portion and an blade receiving portion, the blade receiving portion sized and shaped to receive the circular shaped blade with the sharp edge of the forward portion extending beyond a front surface of the blade holder, the circular shaped blade being secured within the blade receiving portion of the blade holder, the circumferential edge of the blade being configured to cooperate with blade holder to secure the blade and blade holder in a predetermined positional relationship.

16. The blade assembly of claim 15 wherein the blade has a first and a second extension projecting outwardly from the circumferential side edges, and the blade receiving portion of the blade holder has like shaped receiving portions therein.

17. The blade assembly of claim 16 wherein the first and a second extension projecting outwardly from the circumferential side edge are circular in shape.

18. The blade assembly of claim 15 wherein the blade has first and a second indentations through the circumferential side edges and the blade receiving portion of the blade holder has like shaped receiving extensions therein.

19. A blade for a microtome, the blade being generally circular or parabolic in shape and comprising a) a straight front cutting edge,
b) a circumferential side edge extending rearwardly from left and right ends of the front cutting edge, and
c) first and second spaced apart extensions projecting outwardly in the plane of the blade from the circumferential side edge.

20. A blade for a microtome, the blade being generally circular in shape and comprising a) a straight front cutting edge,
b) a circumferential side edge extending rearwardly from left and right ends of the front cutting edge, and
c) first and second spaced apart openings extending inwardly in the plane of the blade from the circumferential side edge.

* * * * *